United States Patent [19]

Soto

[11] 3,991,912

[45] Nov. 16, 1976

[54] FLEXIBLE PACKAGE WITH COUNTER-PRESSURE DISPENSER

[76] Inventor: Ricardo Hurtado Soto, Apartado 91711, Bogota, Colombia

[22] Filed: Jan. 23, 1975

[21] Appl. No.: 543,264

[52] U.S. Cl. .............................. 222/89; 128/214 D; 128/DIG. 24; 215/11 E; 222/81
[51] Int. Cl.² ........................................ A61M 25/00
[58] Field of Search ................. 222/80, 81, 541, 89; 215/11 E; 128/DIG. 24, 272, 214 D

[56] References Cited
UNITED STATES PATENTS

| | | | |
|---|---|---|---|
| 3,255,923 | 6/1966 | Soto | 222/81 X |
| 3,307,549 | 3/1967 | Zackheim | 128/DIG. 24 |
| 3,474,789 | 10/1969 | Soto | 128/272 |

FOREIGN PATENTS OR APPLICATIONS

| | | | |
|---|---|---|---|
| 830,222 | 3/1960 | United Kingdom | 222/81 |

Primary Examiner—Stanley H. Tollberg
Assistant Examiner—David A. Scherbel
Attorney, Agent, or Firm—Dawson, Tilton, Fallon & Lungmus

[57] ABSTRACT

A package includes a sealed collapsible container of puncturable film material with liquid contents. One portion of the container is formed into a pocket. The container is also provided with structure for attachable receiving a dispenser which is adapted to be secured to the receiving structure. The dispenser may be a cannula with an insert or penetration conduit. When the insert conduit is placed in the pocket and forced to penetrate the innermost portion thereof, the body of the dispenser is secured to the receiving structure of the container. Pressure may be applied to the container and contents to dispense the contents through the attached cannula; and this pressure forces the inner folds of the gusset into progressive sealing engagement with the insert conduit of the cannula to prevent spillage or seepage of the liquid contents.

8 Claims, 8 Drawing Figures

FLEXIBLE PACKAGE WITH COUNTER-PRESSURE DISPENSER

BACKGROUND AND SUMMARY

The present invention relates to apparatus for dispensing medicaments or the like; and more particularly, it relates to a sealed package for a liquid medicament and a separate attachable dispenser for use with it.

The invention may be regarded as improving aspects of the devices disclosed in my U.S. Pat. Nos. 3,255,923 and 3,474,789, and in its broader aspects, it includes a sealed collapsible container of puncturable film material in which the medicament is contained. A portion of the container is doubly folded to provide two inner folds defining a pocket. In one embodiment, the periphery of the container is stiffened and holds the pocket material fixed in relation to a dispenser. The stiffened container material also provides a tab in front of the gusset opening defining an aperture or providing equivalent receiving means for a dispenser.

The dispenser may include a cannula and an insert conduit in communication with the cannula. The insert conduit is of sufficient length to pierce the innermost part of the pocket when the dispenser is attached to the container. The dispenser also includes a rivet-like attaching button with a rounded head for being inserted through the aperture on the stiffened tab of the container, thereby securing the dispenser to the container after insertion of the insert conduit through the pocket.

The liquid contents of the container may be dispensed under gravity or under slight hand pressure exerted on the collapsible container, as may be required to overcome resistance or back paressure, for example, in teh case of an intramuscular injection.

One of the important features of the present invention is the means by which the inner folds of the gusset sealingly engage the insert conduit of the dispenser after it penetrates the innermost portion of the pocket. After piercing, the insert conduit is, of course, free to transmit the contents of the container for application or dispensing. As pressure is applied, even the slightest pressure as would be caused by gravity acting on the contents of the container, will cause the inner folds of the pocket to wrap around the inset conduit of the dispenser to prevent seepage through the broken portion of the pocket. As the pressure is increased on the contents, the contact area between these inner folds and the insert conduit and the sealing force will increase progressively, thereby preventing seepage or loss through the punctured location.

Other embodiments of the invention are disclosed for different applications, including variations of the means for attaching the dispenser to the container, and modifications of the dispenser for different applicators.

Other features and advantages of the present invention will be apparent to persons skilled in the art from the following detailed description of a preferred embodiment accompanied by the attached drawing wherein identical reference numerals will refer to like parts in the various views.

THE DRAWING

DETAILED DESCRIPTION

Figure 1:
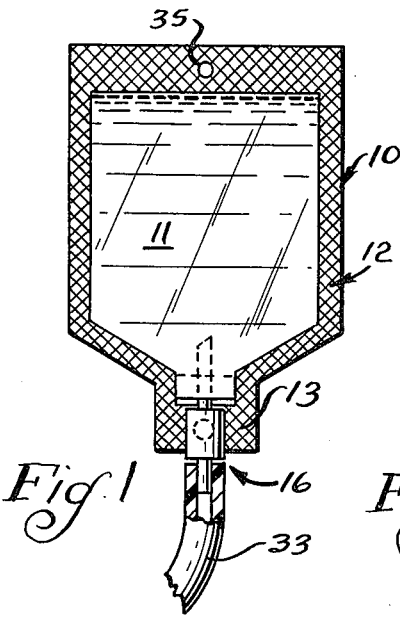
FIG. 1 is a front view of a package with attached dispenser constructed according to the present invention.

Turning first to the embodiment of FIGS. 1–4, reference numeral 10 generally designates a flexible container with liquid contents 11. The container 10 may be formed by laminating two sheets of polyethylene film together having a thickness, for example, of approximately 5 mils. The surrounding border of the container 10 is generally designated 12, and it forms a stiffened, yet collapsible periphery, the lower end of which, designated 13 is sometimes referred to as a tab.

Figure 4:
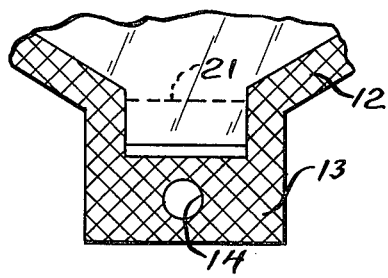
FIG. 4 is a partially cut-away close-up view of the tab portion of the container of FIG. 1.

As best seen in FIG. 4, the tab 13 defines an aperture 14 for attachable receiving a dispenser generally designated by reference numeral 16. Although this embodiment is designed for dispensing medicaments or the like, the term "dispenser" is intended to have a meaning not limited to medical applications, as will be apparent from the other embodiments.

The container 10, when viewed from the side, includes first and second flexible side walls 17, 18. The side wall 17 is doubly folded at its bottom portion, the two folds being designated 19 and 20 in FIG. 2, and thence laminated to the other wall 18 to form the tab 13. The doubly-folded wall provides a pocket having an innermost portion designated 21 in FIGS. 2 and 3. The pocket may be built into the container, or formed by an attachment, or pre-formed at the time of use.

Figure 3:
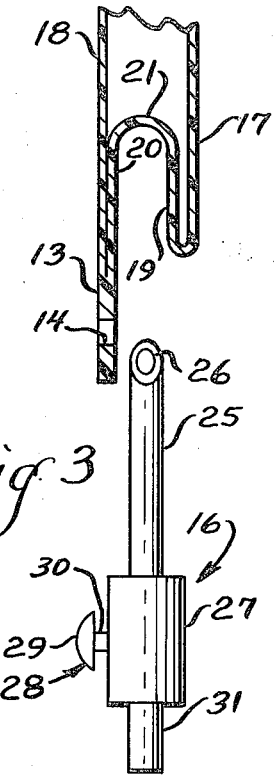
FIG. 3 is a close-up view, similar to FIG. 2, with the container partially cut away, but showing the dispenser prior to insertion and attachment.

As best seen in FIG. 3, the dispenser 16 includes an insert conduit or tube 25 having an inclined tip as at 26 to facilitate piercing of the container material at the base or innermost portion of the socket. An enlarged body portion 27 is provided with a rivet-like attaching member generally designated 28 and including a rounded head member 29 and a neck of reduced diameter designated 30.

At the end of the body portion 27 opposite the insert conduit 25 and in fluid communication with it, there is an external cannula 31 to which a flexible conduit 33 (FIGS. 1 and 2) may be attached, for example, as in the case of a dispenser for saline or plasma. The upper portion of the stiffened border 12 may also be provided with an aperture as at 35 in FIG. 1 for hanging the container during use.

The dispenser 16 may be made of metal or other rigid material, but it may be made of a rigid plastic material such as high-density polyethylene.

The cannula 16 may be packaged separately (in a sterile enviroment for medical applications) for removal prior to use. When it is desired to dispense the contents 11 of the container 10, the dispenser 16 is taken from its container and located approximately in the position shown in FIG. 3. It is then moved axially until the slanted tip 26 pierces the innermost portion 21 of the pocket. The rounded head 29 of the attaching structure 28 is then placed through the aperture 14 on the tab 13 of the flexible container to hold the dispenser in place during use.

Figure 2:
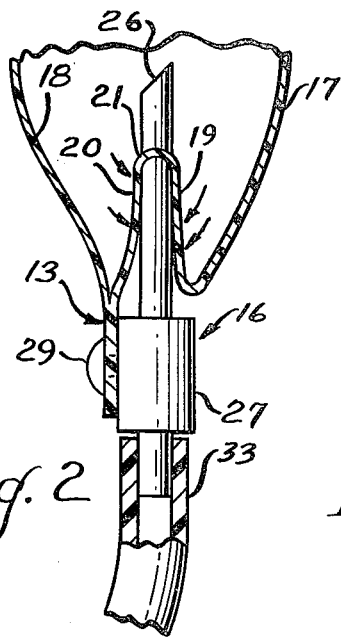
FIG. 2 is a close-up cross sectional view of FIG. 1 showing the attachment of the dispenser and insertion into the container.

Referring particularly to FIG. 2, when the dispenser is attached to the container, and particulary when the application is one in which some resistance must be overcome or a back pressure is created (as in the case of intramuscular injections, for example), it may be desired to induce a pressure on the fluid contents 11 of the container 10 by collapsing the container under hand pressure. The attachment of the cannula 16 to the container 10 resists any tendency to dislodge the dispenser, but more importantly, the flexible nature of the pocket walls 19 and 20, enables them to engage the insert conduit 25 of the cannula and seal against it, the application pressure being transmitted through the fluid contents to the inner surface of the container walls, as indicated diagrammatically by the arrows. Further, the greater the internal pressure, the greater and more progressive will be the sealing area and sealing pressure, thereby preventing loss or spillage, not only during insertion but also during application.

In this as in other embodiments, the limited width of the pocket in relation to the outer diameter of the insert conduit 25 is important in that a narrow mouth of the pocket makes it difficult to insert the dispenser, whereas a wide mouth would permit the inner fold of the pocket to extend outwardly. As an example, if the outer diameter of the insert conduit is 14 mm., the pocket walls should be loose enough to permit easy entry but taut enough to make it difficult to insert a conduit with an outer diameter of 20 mm.

Figure 5:
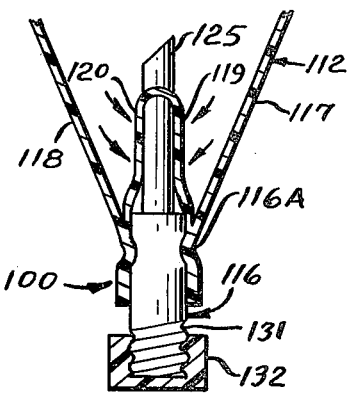
FIG. 5 is a cross sectional view, similar to FIG. 2, of a first modification of the invention.

Turning now to the embodiment of FIG. 5, the flexible walls of a container for flowable contents are designated 117 and 118 respectively, and they are inclined toward a mouth or dispensing location 100. A pocket is formed of flexible interior walls 119 and 120.

A dispenser, generally designated 116 is heat-sealed or crimped as at 116A to the container 112 (either during manufacture or just prior to use).

In this application, the distal end of the dispenser 116 is provided with external threads 131, and a cap 132 is secured to it. The embodiment of FIG. 5 is particularly useful in dispensing pastes. Again, the dispenser is provided with an insert conduit 125 which pierces the innermost portion of the pocket formed by the flexible walls 119, 120.

Figure 6:
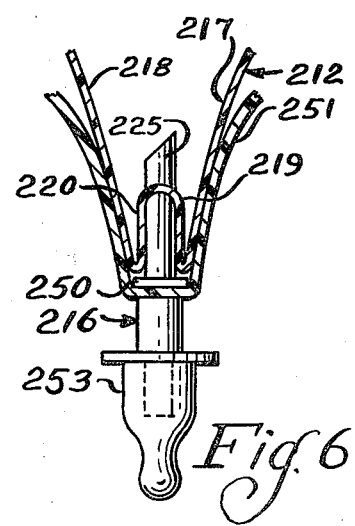
FIG. 6 is a partially broken-away cross sectional view, similar to FIG. 2 of a second modification of the invention.

Turning now to the embodiment of FIG. 6, the flexible side walls of a container generally designated 212 are individually designated 217 and 218 respectively. The inner walls of the pocket are designated 219 and 220. In this embodiment, the dispenser 216 is provided with an enlarged collar 250 over which is received a strip or patch of adhesive or pressure-sensitive tape 251. The dispenser 216 is provided at one end with an insert conduit 225, and at the other end with a nipple 253.

Figure 7:
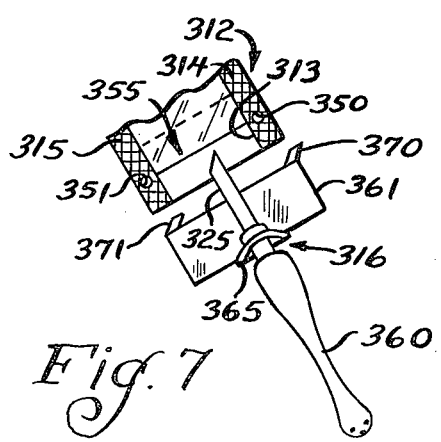
FIG. 7 is a partially broken-away exploded view just prior to piercing, of a third modificaton of the invention.

In the embodiment of FIG. 7, the flexible container is designated 312, and it has an enlarged neck 313 with first and second side borders 314 and 315. Apertures 350 and 351 are provided in the borders 314 and 315 respectively, at locations adjacent the gusset which is generally designated 355.

The dispenser, generally designated 316, includes an insert conduit 325 and an irrigating applicator 360. The dispenser is attached to a rigid body 361 of sheet material by means of a ring bracket 365. The body 361 is provided with side tabs 370, 371, which are received in the apertures 350, 351 respectively, and thence bent backward to secure the attaching dispenser and its holder to the borders of the flexible container adjacent the mouth, after the insert conduit 325 has been inserted into the pocket 355 and pierced the innermost end thereof to dispense the fluid contents of the container.

Figure 8:
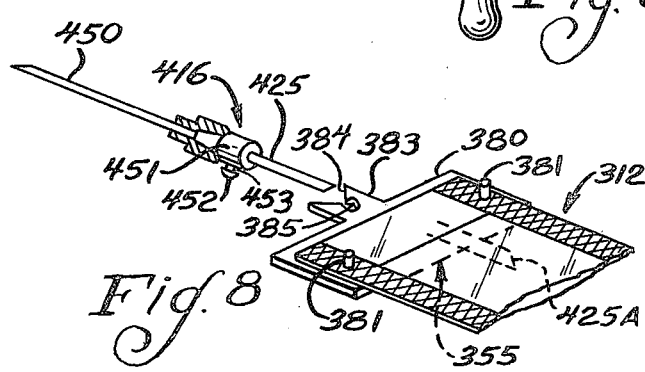
FIG. 8 is a partially broken-away perspective view, with the attaching dispenser again shown in exploded relation just prior to insertion, of a fourth modification of the invention.

In the embodiment of FIG. 8, the container is similar to that shown in FIG. 7 and generally designated 312. In this embodiment, however, a rigid receiving device 380 including bosses 381 is attached to the container 312 adjacent its mouth, and outwardly of the pocket 355. The central outer portion of the member 380 is provided with an extension 383 defining a V-shaped guide surface 384 leading into a receiving mouth 385.

The dispenser is generally designated 416, and it includes an insert conduit 425 and a needle 450. A central body portion 451 is provided with a rivet-like attaching device 452, having a neck 453 which is guided, during insertion, by the guide surfaces 384 into the mouth 385, where it is secured during use. The inserted position of the insert conduit 25 is shown in dashed line, as at 425A in FIG. 8.

In all of the disclosed embodiments, it will be appreciated that the dispenser is attached or secured to the container, and that an insert conduit of the dispenser is received between the inner folds of a pocket formed in the flexible container, the insert conduit of the dispenser piercing the innermost portion of the pocket for dispensing the contents. Further, any back pressure during insertion or any internal pressure exerted on the contents of the container during dispensing will transmit a sealing force to the inner folds of the pocket to progressively wrap the inner folds of the pocket about the insert conduit in sealing, wrapping engagement to prevent loss of contents during insertion and use.

Having thus disclosed in detail a number of embodiments of the invention, each modified to a different application, persons skilled in the art will be able to alter certain of the structure which has been illustrated or substitute equivalent elements for those disclosed while continuing to practice the principle of the invention; and it is, therefore, intended that all such modifications and substitutions be covered as they are embraced within the spirit and scope of the appended claims.

I claim:

1. A package, comprising a sealed, collapsible container of puncturable, flexible material and defining a dispensing location, a portion of said container adjacent said dispensing location being doubly folded to provide two inner folds defining a pocket, said folds being joined at an innermost location; receiving means on said container adjacent said dispensing location; dispenser means detachably securable to said container, and including an insert conduit for insertion between said inner folds of said pocket for penetrating the innermost portion thereof to gain access to said contents of said container, and means on said dispenser for securing said dispenser to said container at said receiving means adjacent said dispensing location; said receiving means on said container providing stiffening means including a stiffened tab portion of said container defining an aperture adjacent said pocket for stiffening said container adjacent said pocket to retain said folded shape even when the contents are subjected to pressure; and means projecting from the body of said dispenser for extending through and coupling with said aperture of said tab portion of said container when said dispenser means is inserted in assembled relation with said container; whereby back pressure during insertion of said dispenser means and hand pressure exerted on said container after insertion will be transmitted to the inner folds of said pocket to force the same together in progressive sealing engagement with said insert conduit to prevent seepage of the contents.

2. A package, comprising a sealed, collapsible container of puncturable, flexible material and defining a mouth adjacent a dispensing location, a portion of said container adjacent said dispensing location being doubly folded to provide two inner folds defining a pocket, having a channel shape and extending across said mouth, said folds being joined at an innermost location; said container including first and second apertures adjacent the ends of said pocket; receiving means on said container adjacent said dispensing location; and dispenser means detachably securable to said container, and including an insert conduit for insertion between said inner folds of said pocket for penetrating the innermost portion thereof to gain access to said contents of said container, and means on said dispenser means for securing said dispenser means to said container at said receiving means adjacent said dispensing location; said dispenser means providing stiffening means for stiffening said container adjacent said pocket to retain said folded shape even when the contents are subjected to pressure and including a rigid base portion with first and second tabs extending therefrom, said tabs registering with the apertures on said container when said dispenser means is assembled thereto in dispensing relation, said dispenser means further comprising means for mounting said insert conduit to said rigid base portion, whereby when said dispenser means is assembled to said container in dispensing relation, the tabs of said base portion of said dispenser means are in register with said apertures of said container and said tabs may be folded backwardly to releasably secure said dispenser means to said container, said insert conduit extending through said pocket and penetrating the innermost portion thereof; whereby back pressure during insertion of said dispenser means or hand pressure exerted on said container after insertion will be transmitted to the inner folds of said pocket to force the same together in progressive sealing engagement with said insert conduit to prevent seepage of the contents.

3. The structure of claim 2 wherein said dispenser means further comprises an irrigation device in fluid communication with said insert conduit and extending from the other end thereof.

4. A package, comprising a sealed, collapsible container of puncturable, flexible material and defining a mouth adjacent a dispensing location and two apertures adjacent said location, a portion of said container adjacent said dispensing location being doubly folded to provide two inner folds defining a pocket, said folds being a pleated portion of a wall of said container extending across said mouth and joined at an innermost location; stiffening means for stiffening said container adjacent said folds to maintain said pocket comprising a stiff attaching member having projections extending through the apertures of said container and including a socket with a lead-in surface; first and second receiving means on the periphery of said container adjacent said dispensing location; and dispenser means detachably securable to said container, and including an insert conduit for insertion between said inner folds of said pocket for penetrating the innermost portion thereof to gain access to said contents of said container, said insert conduit further including a projection adapted to snap into said socket, guided during insertion by lead-in surface and means on said dispenser means for securing said dispenser means to said container at said receiving means adjacent said dispensing location; whereby back pressure during insertion of said dispenser means or hand pressure exerted on said container after insertion will be transmitted to the inner folds of said pocket to force the same together in progressive sealing engagement with said insert conduit to prevent seepage of the contents.

5. The apparatus of claim 4 wherein said dispenser means further comprises a needle extending from the end thereof opposite said insert conduit.

6. A package, comprising a sealed, collapsible container of puncturable, flexible material and defining a dispensing location, a portion of said container adjacent said dispensing location being doubly folded to provide two inner folds defining a pocket, said folds being joined at an innermost location; means for stiffening said container adjacent said folds to maintain said pocket; receiving means on said container adjacent said dispensing location; and dispenser means detachably securable to said container, and including an insert conduit for insertion between said inner folds of said pocket for penetrating the innermost portion thereof to gain access to said contents of said container, and means on said dispenser for securing said dispenser to said container at said receiving means adjacent said dispensing location; said dispenser including rigid connector means releasably secured to said dispenser means and adapted to be releasably secured to said container to provide said stiffening means for stiffening said container adjacent said pocket to retain said folded shape even when the contents are subjected to pressure; whereby back pressure during insertion of said dispenser means or hand pressure exerted on said contaner after insertion will be transmitted to the inner folds of said pocket to force the same together in progressive sealing engagement with said insert conduit to prevent seepage of the contents.

7. A package, comprising a sealed, collapsible container of puncturable, flexible material and defining a dispensing location, a portion of said container adjacent said dispensing location being doubly folded to provide two inner folds defining a pocket, said folds being joined at an innermost location; means releasably secured to said container for stiffening said container adjacent said folds to maintain said pocket; receiving means on said container adjacent said dispensing location; and dispenser means detachably securable to said container, and including an insert conduit for insertion between said inner folds of said pocket for penetrating the innermost portion thereof to gain access to said contents of said container, and means on said dispenser for securing said dispenser to said container at said receiving means adjacent said dispensing location; said stiffening means when secured to said container stiffens said container adjacent said pocket to retain said folded shape even when the contents are subjected to pressure; whereby back pressure during insertion of said dispenser means or hand pressure exerted on said container after insertion will be transmitted to the inner folds of said pocket to force the same together in progressive sealing engagement with said insert conduit to prevent seepage of the contents.

8. A package, comprising a sealed, collapsible container of puncturable, flexible material and defining a dispensing location, a portion of said container adjacent said dispensing location being doubly folded to provide two inner folds defining a pocket, said folds being joined at an innermost location; means for stiffening said container adjacent said folds to maintain said pocket; receiving means on said container adjacent said dispensing location; and dispenser means detachably securable to said container, and including an insert conduit for insertion between said inner folds of said pocket for penetrating the innermost portion thereof to gain access to said contents of said container, and means on said dispenser for securing said dispenser to said container at said receiving means adjacent said dispensing location; said stiffening means being fixed to said dispenser means for stiffening said container adjacent said pocket to retain said folded shape even when the contents are subjected to pressure; whereby back pressure during insertion of said dispenser means or hand pressure exerted on said container after insertion will be transmitted to the inner folds of said pocket to force the same together in progressive sealing engagement with said insert conduit to prevent seepage of the contents.

* * * * *